United States Patent [19]

Odén et al.

[11] Patent Number: 5,080,589
[45] Date of Patent: Jan. 14, 1992

[54] ARTIFICIAL TOOTH CROWNS

[75] Inventors: Agneta E. Odén, Stocksund; Hans T. Rostvall, Hägersten, both of Sweden

[73] Assignee: Sandvik AB, Sandviken, Sweden

[21] Appl. No.: 453,977

[22] Filed: Dec. 20, 1989

[30] Foreign Application Priority Data

Dec. 20, 1988 [SE] Sweden .................. 8804588

[51] Int. Cl.$^5$ .................. A61C 13/08; A61C 5/08
[52] U.S. Cl. .................. 433/202.1; 433/218
[58] Field of Search ........... 433/202.1, 212.1, 218, 433/222.1, 223

[56] References Cited

U.S. PATENT DOCUMENTS

| 4,321,042 | 3/1982 | Scheicher | 433/212.1 X |
| 4,431,420 | 2/1984 | Adair | 433/201.1 X |
| 4,451,236 | 5/1984 | Tarasov et al. | 433/207 |
| 4,548,959 | 10/1985 | Nagai et al. | 433/212.1 X |
| 4,585,417 | 4/1986 | Sozio et al. | 433/222.1 X |
| 4,747,876 | 5/1988 | Hakamatsuka et al. | 433/222.1 X |
| 4,793,809 | 12/1988 | Sigler et al. | 433/222.1 X |
| 4,909,738 | 3/1990 | Ai et al. | 433/218 X |

FOREIGN PATENT DOCUMENTS 2552317  8/1976  Fed. Rep. of Germany ...... 433/218

Primary Examiner—Robert P. Swiatek
Assistant Examiner—Todd E. Manahan
Attorney, Agent, or Firm—Burns, Doane, Swecker & Mathis

[57] ABSTRACT

The present invention relates to an artificial tooth crown composed of a prefabricated coping designed for artificial strength densely sintered ceramic material with powder metallurgical methods. The tooth crown is given the final shape by a veneer material attached to the external surface of the coping by e.g., firing or dental porcelain. The tooth crown can be made in less manufacturing time with an increase in the strength and the accuracy to shape.

11 Claims, 1 Drawing Sheet

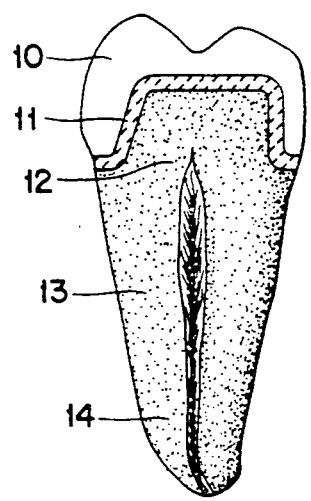
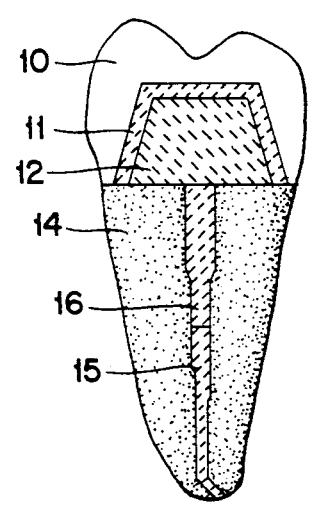
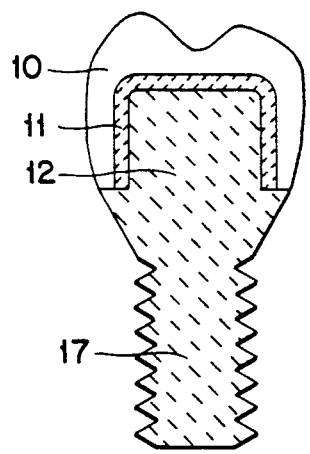
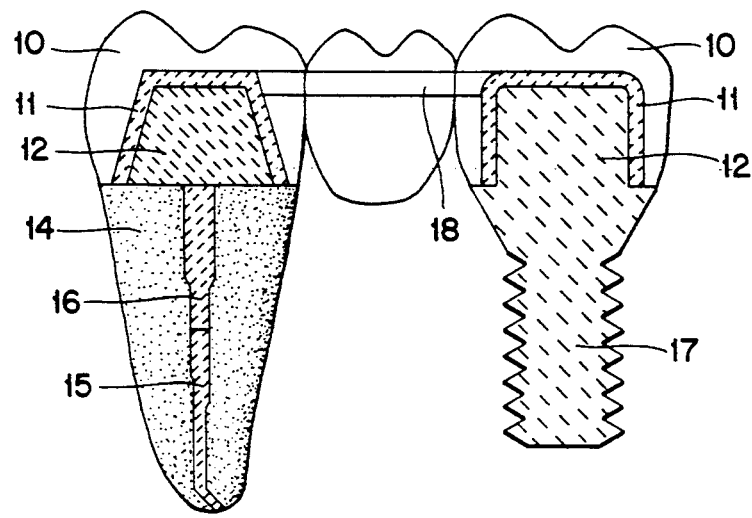

ARTIFICIAL TOOTH CROWNS

BACKGROUND OF THE INVENTION

This invention relates to accurately shaped artificial, all ceramic tooth crowns for dental prosthetic constructions. By starting from a prefabricated coping, a tooth crown is obtained which is easier to produce and therefore of lower cost. In addition, the crown has higher strength and a more accurate shape. Preferably the coping is manufactured from a biocompatible, high strength, ceramic material, which is sintered to high density.

U.S. Pat. No. 4,575,340 describes a prefabricated abutment used in combination with a prefabricated sleeve-like coping telescopically mated to the abutment. This coping is made by a known lost-wax method of a precious or non-precious metal.

Artificial tooth crowns are today manufactured mainly in the following way: A dentist makes a preparation on a tooth, on which a tooth crown is to be fixed in the mouth of a patient, an impression is made and with this impression a copy of the preparation is made in gypsum. On this model, a dental technician prepares a crown of wax. The adjacent teeth must be considered, and the dental technician must have models from the two jaws. A sprue former in wax is fixed on one of the cusps of the wax crown. The wax crown is loosened from the gypsum model. The wax crown with the sprue former are invested in a metal ring with investment. The wax is burnt out and a crown can be cast in a precious or non-precious metal. The cast crown can, in certain cases, be covered by a veneer made of porcelain in order to obtain a tooth crown color similar to the color of natural teeth. Instead of porcelain, plastic material can be used.

The fabrication of tooth crowns in glass is very close to the technique described above with the difference that after the casting, a thin layer of porcelain is painted on the surface and fired in order to give the tooth crown individual tooth colors.

Tooth crowns fabricated mainly of porcelain can be made with conventional dental porcelain technique from a sheet made of a precious or non-precious alloy. Porcelain crowns can also be made with conventional dental porcelain technique on a model of the abutment. The material of this model does not change dimensions on heating up to 1200° C. When the tooth crown is ready the model of the abutment is removed by sand blasting.

The above described complicated and time consuming methods are today used to manufacture crowns, which will fit on individually prepared natural teeth, on prefabricated abutments for implants, and on prefabricated pins for anchoring of tooth crowns to root filled teeth.

The problem with the material now used (porcelain, glass, etc.) in artificial tooth crowns is their brittleness, which often leads to early fracture. These artificial crowns must be replaced more or less regularly.

OBJECTS AND SUMMARY OF THE INVENTION

The object of the present invention is to provide an artificial, all ceramic tooth crown, which is easier and accordingly cheaper to made with higher strength and more accurate shape.

Another object is to make a crown by using a densely sintered, high strength ceramic material, combining the demands for high strength and accurate shape with the demands for the successful application of porcelain.

In accordance with the present invention, there is provided an artificial tooth crown which comprises a coping and a veneer in which the coping is prefabricated of a biocompatible ceramic material having a relative density of greater than 98 percent.

BRIEF DESCRIPTION OF THE DRAWINGS

FIG. 1 is a schematic representation of an artificial tooth crown on a natural root.

FIG. 2 is a schematic representation of an artificial tooth crown on a filled root.

FIG. 3 is a schematic representation of an artificial tooth crown on an implant.

FIG. 4 is a representation of an artificial tooth crown used in bridge construction.

DETAILED DESCRIPTION OF THE PREFERRED EMBODIMENTS

FIG. 1 shows an alternative design of an artificial tooth crown on a natural root. In the figure, the veneer is indicated as 11, the coping as 11, the abutment as 12, the pulp as 13 and the natural tooth root as 14.

In the other alternative designs shown in FIG. 2 for a filled root, and FIG. 3 for an implant and in FIG. 4 for bridge construction, the same letters mean the same things as with FIG. 1 while a root filling is indicated as 15 (FIGS. 2 and 4), 16 is an endodontic post (FIGS. 2 and 4), 17 is a root implant (FIGS. 3 and 4) and 18 is a beam with a pontic (FIG. 4).

In each of the Figures, the artificial tooth crowns are the combination of the coping 11 with the veneer 10. They are fixed on the abutment 12 with cement or by a mechanical joint.

According to the present invention, artificial tooth crowns are made in which the coping is prefabricated from a biocompatible material with an internal cavity given such dimensions as to fit on an abutment, which can be a part of an implant, a root canal pin or a part of a bridge. A biocompatible material for copings is a material which is not toxic and does not cause damage on oral tissues or does not give unwanted system effects. In addition, this material must not discolor or otherwise give unwanted effects to the veneer material. The crown is fixed by cementation or by a mechanical joint, e.g., screw joint.

The present invention allows a considerable simplification of the handicraft of the dental technician. With the aid of gypsum models of the two jaws and with the prefabricated coping on the model of the abutment, a dental technician can make the final design of the tooth crown and at the same time control its function and size. In order to make the veneer, a porcelain furnace or an apparatus for pressing of composite veneer is needed. The method of making a tooth crown to fit an existing abutment according to the present invention decreases essentially the time of production for tooth crowns and at the same time increases its strength and accuracy of shape.

The coping is preferably made from a densely sintered, high strength ceramic material made by powder metallurgical techniques. It has been found that it is possible to compact and sinter a ceramic powder directly for use as a coping in artificial tooth crowns. The pressed coping may be ground before sintering so as to minimize the amount of adjustments to be made after it is sintered and to preferably form a coping which may be directly used with little or no adjustments in artificial tooth crowns. Once the coping is obtained, the veneer may be built up so that the final product will be a tooth crown which can be fitted to existing abutments and/or to the actual set of teeth.

The ceramic powder can be made by several well known methods. Traditional powder metallurgical techniques can be used, where the different components are mixed and ground under dry or wet conditions with water or an inorganic solvent (e.g., alcohols) as grinding liquid. The so-called SOL-GEL technique can also be used where different oxide materials are deposited together from a water solution or are co-precipitated from metal alcoxides in e.g, water free alcohol by controlled addition of water. A combination of different techniques can also be used by using SOL-GEL technique to deposit a surface layer of desired metal oxide on a powder material. Lubricants or other organic binders depending on the choice of forming method may be added to the ceramic powder when needed at suitable times in the process as is conventionally known. Other preparation routes of the ceramic material are also possible such as, reaction sintering where a suitable metal is oxidized, nitrided, etc. For example, aluminium-/alumina can be oxidized under carefully controlled processing to alumina. These methods allows preforming or reinforcement by fibers, e.g., in a felt infiltrated with liquid metal.

Many of the monolithic ceramics which are biocompatible may have a brittle performance if they are not sintered to nearly full density, more than 98% and preferably >99.5% of the theoretical density. However, these ceramics can be strengthened by a number of toughening mechanisms. Finely dispersed particles, platelets, whiskers or fibers raise the fracture toughness of the composite. Typical additives are the nitrides, carbides, borides or mixtures thereof of the transition metal oxides of group IV-VI or of the elements Al or Si. Toughening may also be achieved by so called transformation toughening, i.e., additions of unstabilized $ZrO_2$ or $ZrO_2$ stabilized with $Y_2O_3$, MgO or CaO. The additions of these latter oxides shall not exceed 25 wt %, but should be more than 2 wt %. The best performance is obtained with 3-12 wt % of the $ZrO_2$.

The powder with lubricants and/or other organic binders is cold isostatically compacted, uniaxially pressed, slip cast, pressure cast, injection molded or compacted in another suitable way. The compacted body has such dimensions that after the shrinking during the subsequent sintering process to high density, it has the desired final geometrical shape with great accuracy. It is important that the ceramic material is sintered to closed porosity, which for an oxide material means at least 95% of theoretical density. In order to assure good mechanical strength, the material should preferably have a density over 98% of theoretical density, while density over 99.5% give the best strength.

The sintering can take place in a vacuum, under normal atmospheric pressure or under increased pressure in connection with the overpressure sintering of hot isostatic compaction or alternatively by hot pressing. Pure oxide material can be sintered in air, but some composites have to be sintered in inert or controlled atmosphere. The coping is given an external shape so that the following build-up of the veneer is facilitated. The external shape can be, e.g., cylindrical or slightly cone-shaped. The cross section can be, e.g., circular, oval or angular. The shape can also be such that it is roughly similar to natural teeth. If dental porcelain is used as the veneer with a coefficient of thermal expansion adapted to the material of the coping, the porcelain will adhere better. In the case of $Al_2O_3$ as the coping material, there will be a "chemical bond" between $Al_2O_3$ and porcelain. This means that the external surface of the coping does not need any retention elements. When using other veneer materials such as plastic, mechanical retention elements can be needed, e.g., grooves, pits or sintered retention elements on the coping.

Preferably, the ceramic copings are made in large scale production by uniaxial compaction. In that process, a mandrel is used of the size and shape of the artificial abutment on which the crown will fit. The mandrel, which can be made from a hardenable steel and is hardened after manufacturing, has such a size that the coping after the sintering shrinkage will have the desired fit to the natural or artificial abutment in question. During the compaction, the mandrel is placed on an ejector and will give the internal shape to the coping which will fit to the prefabricated abutment. The external shape of the coping can be made during the compaction by the upper and lower punches, but the external shape can also be made by grinding, preferably before sintering.

The ceramic base material in the coping comprises preferably one or several biocompatible oxides (including phosphates, silicates and sulfates), with the additives of carbides, silicides, nitrides or borides with or without binder metal (preferably iron-group metals) in addition to conventional sintering aids. The base material can also comprise other biocompatible high performance ceramics such as nitrides, oxynitrides, carbides, etc. Examples of the two former materials are $Si_3N_4$, $Si_2N_2O$, sialon, AlN, AlON, etc. Examples of biocompatible oxides which can form the base matrix for the ceramic body, are $Al_2O_3$, $TiO_2$, MgO, $ZrO_2$, and $ZrO_2$ (partly or totally stabilized with amounts of up to 25 weight % of $Y_2O_3$, MgO or CaO).

Also, components such as SiC, TiN, TiC, $TiB_2$, $Si_3N_4$, or other biocompatible carbides or nitrides of group IV, V or VI can be present as particles with a size of <25 μm, preferably <10 μm and/or as whiskers (hair shaped single crystals) with a length to diameter ratio >5, preferably >10 and/or fibers (polycrystalline) with a diameter of >10 μm and/or as single crystal platelets with an approximate diameter of 5-50 μm, preferably 5-20 μm and a thickness of 1-10 μm, preferably 1-4 μm. The amount of whiskers, fibers and/or platelets should not exceed 60 volume %, preferably less than 40 vol %.

In a preferred embodiment, the ceramic material comprises >50%, preferably >85%, by weight of $Al_2O_3$ with additives of conventional sintering aids. In order to increase the strength, <25 weight %, preferably 3-12 weight %, of $ZrO_2$, and/or 5-40 weight %, preferably 10-30 weight % of SiC whiskers can be added. In order to get a suitable color, colored components can be chosen. For example, 0.1-10 weight %, preferably 0.5-5 weight %, of TiN and/or ZrN will give $Al_2O_3$ based copings a faint yellow shade.

For some purposes, it can be suitable to coat the coping before the veneering with at least one thin layer of 1-10 μm of $Al_2O_3$ or TiN. The coating is performed by known techniques e.g., Chemical Vapor Deposition (CVD) or Physical Vapor Deposition (PVD).

The invention is additionally illustrated in connection with the following Example which is to be considered as illustrative of the present invention. It should be understood, however, that the invention is not limited to the specific details of the Example.

EXAMPLE

Copings to fit an abutment with a hexagonal shape of titanium for implants, height=4 mm and distance between parallel sides=3.3 mm, were uniaxial compacted against a mandrel with a shape uniform to the abutment The mandrel had such a size that it allowed a shrinkage of 17% during the sintering. It was placed as ejector to a cylindrical tool with a diameter of 6.2 mm. The powders used for the compaction had the approximate composition (a) 95.75 weight % of $Al_2O_3$, 4 weight % of $ZrO_2$ and 0.25 weight % of MgO and (b) 99.75% of $Al_2O_3$ and 0.25% of MgO, resp. The sintering was performed in air during 2 hours at 1600° C. After sintering, the blanks had a relative density of 99.5% and the following external dimension: diameter=5.1 mm and height=8.9 mm. The blanks were ground cylindrical with mandrel down to a diameter of 4.8 mm and commercially available dental porcelain was fired on the surface. The first layer of porcelain contained about 50% $Al_2O_3$ and was fired at 1150° C. during 15 minutes. During the heating, the furnace was under vacuum, but when the final firing temperature was reached the firing was preformed under atmospheric pressure. The remainder of the crown was fired at 1050° C. The dental porcelain combined chemically with the alumina without any gap between the porcelain and the densely sintered coping. The crowns fitted perfectly on the abutment and were ready to be cemented with conventional methods on abutment in the mouth of a patient.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

We claim:

1. Artificial tooth crown comprising a coping and a veneer wherein the coping is prefabricated of a sintered biocompatible ceramic material which shrinks during sintering, has a sintered relative density of >98% and wherein the ceramic material comprises >50% by weight of $Al_2O_3$.

2. The artificial tooth crown of claim 1 wherein the biocompatible ceramic material has a relative density of >99.5%.

3. The artificial tooth crown according to claim 1 wherein the ceramic material also includes one or more oxides of the group consisting of $TiO_2$, MgO, $ZrO_2$ or $ZrO_2$ stabilized with up to 10 mol % $Y_2O_3$, or CaO.

4. The artificial tooth crown of claim 1 wherein the $Al_2O_3$ is present in an amount >85% by weight.

5. The artificial tooth crown according to claim 1 wherein the coping also comprises whiskers and/or particles of SiC, TiN, $ZrO_2$ and/or ZrN.

6. The artificial tooth crown according to claim 5 wherein $ZrO_2$ is present in an amount of from 3-12 weight %.

7. The artificial tooth crown according to claim 5 wherein SiC single crystal whiskers are present in an amount of from 10-30 weight %.

8. The artificial tooth crown according to claim 1 wherein the coping is coated with a layer of from 1-10 μm of $Al_2O_3$ or TiN.

9. The artificial tooth crown according to claim 1 wherein the coping contains from 0.1-10 weight % of TiN and/or ZrN.

10. The artificial tooth crown according to claim 9 wherein the coping contains from 0.5-5 weight % of TiN and/or ZrN.

11. The artificial tooth crown according to claim 1 wherein the ceramic material comprises at least 50 weight % $Al_2O_3$, <25 weight % $ZrO_2$ and from 5-40 weight % of SiC single crystal whiskers.

* * * * *